United States Patent
Peiris et al.

(10) Patent No.: US 9,289,571 B2
(45) Date of Patent: Mar. 22, 2016

(54) BREATHING ASSISTANCE APPARATUS

(75) Inventors: Malik Tivanka Rajiv Peiris, Auckland (NZ); Andrew Robert Donald Somervell, Auckland (NZ); Jonathan David Harwood, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 806 days.

(21) Appl. No.: 13/513,174

(22) PCT Filed: Nov. 30, 2010

(86) PCT No.: PCT/NZ2010/000234
§ 371 (c)(1),
(2), (4) Date: Aug. 3, 2012

(87) PCT Pub. No.: WO2011/068418
PCT Pub. Date: Jun. 9, 2011

(65) Prior Publication Data
US 2012/0291783 A1    Nov. 22, 2012

Related U.S. Application Data

(60) Provisional application No. 61/265,498, filed on Dec. 1, 2009.

(51) Int. Cl.
*A61M 11/00* (2006.01)
*A61M 16/10* (2006.01)
(Continued)

(52) U.S. Cl.
CPC ....... *A61M 16/1075* (2013.01); *A61M 16/0051* (2013.01); *A61M 16/0069* (2014.02);
(Continued)

(58) Field of Classification Search
USPC ................ 128/204.18, 204.21, 204.23
See application file for complete search history.

(56) References Cited

U.S. PATENT DOCUMENTS

| 5,551,419 | A | 9/1996 | Froelich et al. |
| 2004/0118403 | A1 | 6/2004 | O'Connor et al. |
| 2005/0268916 | A1 | 12/2005 | Mumford et al. |
| 2007/0062531 | A1 | 3/2007 | Fisher et al. |
| 2007/0193583 | A1 | 8/2007 | Reed |
| 2009/0241958 | A1 | 10/2009 | Baker, Jr. |

FOREIGN PATENT DOCUMENTS

| EP | 0602734 A1 | 6/1994 |
| EP | 2106818 A1 | 10/2009 |

(Continued)

OTHER PUBLICATIONS

International Search Report; International application No. PCT/NZ2010/000234; dated Feb. 24, 2011; 4 pages.

(Continued)

*Primary Examiner* — Steven Douglas
(74) *Attorney, Agent, or Firm* — Knobbe, Martens, Olson & Bear LLP

(57) ABSTRACT

Breathing assistance apparatus includes a gases supply unit adapted to, in use, deliver a stream of pressurised gases from an outlet. The gases supply unit is adapted to vary the pressure of the stream of pressurised gases. A supply path includes a flexible self-supporting gases transportation pathway having a first end connected to the outlet so that the gases transportation pathway receives the stream of gases and conveys the gases to a patient. A patient interface is connected to the second end of the gases transportation pathway receives a stream of gases. At least one sensor measures at least one information parameter of the supply path. A control system associated with the gases supply unit receives the information parameter. The control system contains reference data, and compares the received data to reference data, and determines a supply path based on the comparison.

29 Claims, 6 Drawing Sheets

(51) Int. Cl.
*A61M 16/00* (2006.01)
*A61M 16/16* (2006.01)
*A61M 16/06* (2006.01)

(52) U.S. Cl.
CPC ......... *A61M16/109* (2014.02); *A61M 16/1095* (2014.02); *A61M 16/16* (2013.01); *A61M 16/06* (2013.01); *A61M 16/0666* (2013.01); *A61M 2016/0027* (2013.01); *A61M 2016/0033* (2013.01); *A61M 2205/14* (2013.01); *A61M 2205/3368* (2013.01); *A61M 2205/3553* (2013.01); *A61M 2205/3584* (2013.01); *A61M 2205/3592* (2013.01); *A61M 2205/52* (2013.01); *A61M 2205/6018* (2013.01); *A61M 2205/70* (2013.01); *A61M 2205/702* (2013.01)

(56) References Cited

FOREIGN PATENT DOCUMENTS

| WO | WO 2008/091164 A1 | 7/2008 |
| WO | WO 2009/145646 | 9/2009 |

OTHER PUBLICATIONS

Written Opinion of the ISA; International application No. PCT/NZ2010/000234, dated Feb. 24, 2011, 11 pages.

Office Action for Australian Appl. No. 2010327420 dated Apr. 29, 2015 in 4 pages.

Supplementary European Search Report for European Appl. No. 10834816 dated Jan. 23, 2015 in 6 pages.

BREATHING ASSISTANCE APPARATUS

FIELD OF THE INVENTION

The present invention relates to apparatus that provides a supply of pressurised gas to a recipient via the nasal passages. The present invention also relates to a blower unit that forms part of an apparatus that provides a supply of pressurised gas to a recipient via the nasal passages.

SUMMARY OF THE PRIOR ART

The delivery of a stream of gases to the airways of a patient for the purposes of therapy such as CPAP therapy is well-known. In CPAP therapy, a stream or flow of gases is delivered at a pressure above atmospheric to the airways of a user or patient. In this type of therapy, the intention is that the pressure at the point of delivery is constant, or as close to constant as is possible in a dynamic system where a user is inhaling and exhaling. The (constant) pressure to be provided by the system is usually prescribed by a health professional for any given individual patient or user. The gases stream is usually generated by a blower unit, which is adjustable to provide the desired pressure and flow. A conduit is connected to the output of the blower unit, and the gases are delivered to a user via an interface connected to the other end of the conduit.

There are a number of different blower units on the market which can generate and deliver a stream of breathing gases at an elevated pressure. For example, the S8 AutoScore II™ from ResMed, the SleepStyle™ 600 series from Fisher & Paykel Healthcare, or the Sleep-easy or M-Series from Respironics.

There are also a large number of different interface types which can be used to deliver the stream of pressurised gases to the airways of a user. A 'full-face' mask, which covers and seals around a perimeter enclosing the mouth and nose can be used. A 'nasal mask' covering and sealing around the nose only can also be used. A pair of 'nasal pillows' can also be used, one of each of the pair sealing against the perimeter of the nostrils.

It is normal for a manufacturer such as ResMed, Respironics, or Fisher and Paykel to design and manufacture a small or limited number of different CPAP blowers, and to design these or adapt these so that they can be used with a large number of different types of interface. Comparatively, it is easier to manufacture interfaces and conduits than it is blower units, which are more complex and heavier. It therefore makes sense from a manufacturer's perspective that one blower can be used with a large number and variety of hoses and interfaces. It also makes sense from a user's perspective, as they may wish to use two or more different interfaces with one blower, depending on how their therapy progresses. It is cheaper and easier for a patient to obtain a new hose unit and interface than it is to obtain a new blower unit.

For example, one single type of blower unit could be used with a nasal mask, a full face mask, or nasal pillows, with the output being adjusted for both the type of interface used, and also the particular requirements of the individual user.

As well as changing or swapping the type of interface used, it is common to change or swap the hose or conduit connecting between the blower unit and the interface. Different types of therapy may be delivered more efficiently, with, for example, hoses of different internal diameters.

As can be seen from the above, there are a large number of possible combinations or permutations of equipment. A single blower unit could be suitable for use with a number of different types of interface, and also a number of different types of conduit. As a single blower unit is used with a number of different components and combinations of components, the task of adjusting the blower output to an output which is suitable for that particular combination of elements becomes increasingly complex. A number of different methods for automating this process have been described in the prior art, so that a user does not have to manually make the appropriate adjustments.

For example, WO 06/019323 describes a system which has a conduit which includes a thermistor as part of the electrical circuit. The specification states that " . . . the choice of a particular thermistor value for use with the circuit allows identification by the control system . . . and matching of that thermistor value with a specific conduit . . . upon connection of the conduit to a humidifier or blower device, the control system can identify that thermistor and apply the appropriate control strategy . . . ".

WO 06/092001 describes a conduit that has a resistive electronic component supported by the conduit to provide an identifying feature unique to a specific peripheral component attachable to a flow generator. The resistive component is communicatable to the flow generator so that appropriate operating parameters of the flow generator may be automatically selected by the flow generator to coordinate with the specific peripheral component.

US 2007/0144519 describes a system where components of a CPAP apparatus include a remotely-readable RFID identification tag which is encoded with component identification data. The flow generator or blower receives data derived from the tag, and adapts functions to co-ordinate with this component.

US2004/0074495 discusses calibrating a blower so that it holds characteristics for common masks and hose systems in its memory, or in a remote memory such as a memory card. Additionally, the removable memory can be used to hold other information such as that provided by a health professional. When a user is provided with a different mask/hose or type of mask or hose, they are provided with a card that contains the relevant data. The user inserts the card into the blower unit and apparatus reconfigures itself.

US 2009/0107498 describes a system where patient respiratory requirements are loaded into a respiratory device. The output produced by the respiratory device is then continuously monitored and adjusted according to the patient respiratory.

US2007/0193583 describes switching between two operating modes. The switching has to be manually triggered by a user entering a pin number or inserting a data card or similar.

SUMMARY OF THE INVENTION

It is an object of the present invention to provide a breathing assistance apparatus, or components of a breathing assistance apparatus, that go some way towards overcoming disadvantages of the prior art, or which at least provide users with a useful choice.

In a first aspect the invention may be said to broadly consist in breathing assistance apparatus, comprising:

a gases supply unit adapted to, in use, deliver a stream of pressurised gases from an outlet, said gases supply unit further adapted to vary the pressure of said stream of pressurised gases;

a supply path including a flexible self-supporting gases transportation pathway having an open first end and an open second end, said first end and said outlet adapted to connect in use so that said gases transportation pathway receives said stream of gases and conveys said gases to a patient, and a patient interface connected to said second end of said gases transportation pathway in use and adapted to receive said stream of gases and supply said patient with said gases;

at least one sensor to measure at least one information parameter of a flow of gases in said supply path, a control system associated with the gases supply unit, adapted to receive said at least one information parameter from said at least one sensor, said control system containing reference data, said control system comparing said received data to reference data, and determining a supply path based on said comparison.

According to a further aspect said control system adjusts an operating parameter based on the determined supply path.

According to a further aspect said control system adjusts the operating parameter between a condition suitable for open CPAP and a condition suitable for closed CPAP.

In a further aspect the invention may broadly be said to consist in breathing assistance apparatus comprising:

a gases supply unit adapted to, in use, deliver a stream of pressurised gases from an outlet, said gases supply unit further adapted to vary the pressure of said stream of pressurised gases;

a supply path including a flexible self-supporting gases transportation pathway having an open first end and an open second end, said first end and said outlet adapted to connect in use so that said gases transportation pathway receives said stream of gases and conveys said gases to said patient, and a patient interface connected to said second end of said gases transportation pathway in use and adapted to receive said stream of gases and supply said patient with said gases;

at least one sensor to measure at least one information parameter relating to said supply path, a control system associated with the gases supply unit, adapted to receive said at least one information parameter from said at least one sensor, said control system containing reference data, said control system comparing said received data to reference data, and based on said comparison, adjusting an operating parameter among a condition suitable for open CPAP and a condition suitable for closed CPAP.

According to a further aspect said information parameter is a parameter of a flow of gases in the supply path.

According to a further aspect said control system records data representative of said determined supply path.

In a further aspect the invention may broadly be said consist in breathing assistance apparatus comprising:

a gases supply unit adapted to, in use, deliver a stream of pressurised gases from an outlet, said gases supply unit further adapted to vary the pressure of said stream of pressurised gases;

a supply path including a flexible self-supporting gases transportation pathway having an open first end and an open second end, said first end and said outlet adapted to connect in use so that said gases transportation pathway receives said stream of gases and conveys said gases to said patient, and a patient interface connected to said second end of said gases transportation pathway in use and adapted to receive said stream of gases and supply said patient with said gases;

at least one sensor to measure at least one information parameter of said supply path, a control system associated with the gases supply unit, adapted to receive said at least one information parameter from said at least one sensor, said control system containing reference data, said control system comparing said received data to reference data, determine a supply path based on said comparison, and record data representative of said determined supply path.

According to a further aspect said control system adjusts an operating parameter based on the determined supply path.

According to a further aspect said control system adjusts the operating parameter between a condition suitable for open CPAP and a condition suitable for closed CPAP.

According to a further aspect said information parameter is a parameter of a flow of gases in the supply path.

In a further aspect the invention may broadly be said to consist in breathing assistance apparatus comprising:

a gases supply unit including a fan for producing a stream of pressurised gases, an outlet for supplying, in use, the pressurised gases stream to a supply path including a flexible self-supporting gases transportation pathway and a patient interface;

a control system associated with the gases supply unit adapted to receive at least one information parameter of a flow of gases from said outlet from at least one sensor, said control system containing reference data, said control system comparing said received data to reference data, and determining a supply path based on said comparison.

According to a further aspect said control system adjusts an operating parameter based on the determined supply path.

According to a further aspect said control system adjusts the operating parameter between a condition suitable for open CPAP and a condition suitable for closed CPAP.

In a further aspect the invention may broadly be said to consist in breathing assistance apparatus comprising:

a gases supply unit including a fan for producing a stream of pressurised gases, an outlet for supplying, in use the pressurised gases stream to a supply path including a flexible self-supporting gases transportation pathway and a patient interface;

a control system associated with the gases supply unit, adapted to receive said at least one information parameter of a supply path connected to said outlet from at least one sensor, said control system containing reference data, said control system comparing said received data to reference data, and based on the comparison, adjusting an operating parameter among a condition suitable for open CPAP and a condition suitable for closed CPAP.

According to a further aspect said information parameter is a parameter of a flow of gases in the supply path.

According to a further aspect said control system records data representative of said determined supply path.

In a further aspect the invention may broadly be said to consist in breathing assistance apparatus comprising:

a gases supply unit including a fan for producing a stream of pressurised gases, an outlet for supplying, in use the pressurised gases stream to a supply path including a flexible self-supporting gases transportation pathway and a patient interface;

a control system associated with the gases supply unit, adapted to receive said at least one information parameter of a supply path connected to said outlet from at least one sensor, said control system containing reference data, said control system comparing said received data to reference data, determine a supply path based on said comparison, and record data representative of said determined supply path.

According to a further aspect said control system adjusts an operating parameter based on the determined supply path.

According to a further aspect said control system adjusts the operating parameter between a condition suitable for open CPAP and a condition suitable for closed CPAP.

According to a further aspect said information parameter is a parameter of a flow of gases in the supply path.

According to a further aspect said at least one information parameter includes a heater parameter of the gases supply path According to a further aspect the heater parameter is electrical resistance of a heater of the supply path.

According to a further aspect said control system is adapted to adjust the output of said gases supply unit according to said comparison and a programmable instruction criteria is satisfied.

According to a further aspect said instruction criteria relates to a treatment efficacy parameter.

According to a further aspect said instruction criteria is satisfied when a treatment period has elapsed.

According to a further aspect said instruction criteria relates to a treatment parameter or compliance parameter.

According to a further aspect said programmable instruction criteria is adjustable from a remote location.

According to a further aspect said satisfying said programmable instruction criteria allows said control system to adjust said operating parameter according to said combination of gases transportation pathway and patient interface determined.

According to a further aspect said control system provides a user alert when programmable instruction criteria is not satisfied.

According to a further aspect said programmable instruction criteria can be manipulated by entering a unique code to said control system.

According to a further aspect said stored information about said supply path is indicative of elapsed time of use of one or more types of the determined supply path.

According to a further aspect said stored information is indicative of the time and date the output of said gases supply unit output is adjusted.

According to a further aspect said stored information is indicative of a proportion of time a determined supply path is used.

According to a further aspect said control system is adapted to store information indicative of sleep disordered breathing events including one or more of an apnoea, hyperpnoea, respiratory related arousals, flow limitation, or wake from sleep event, associated with each determined supply path.

According to a further aspect said at least one information parameter includes a parameter indicative of the output pressure of said gases supply unit.

According to a further aspect at least one information parameter includes a parameter indicative of the output gas flow rate of said gases supply unit.

According to a further aspect at least one information parameter includes a parameter indicative of the motor speed of said gases supply unit, or the motor current of said gases supply unit.

According to a further aspect said reference information includes a statistically informative measure of flow for a pressure over a time period.

According to a further aspect said reference information includes a statistically informative measure of pressure for a flow over a time period.

According to a further aspect said statistically informative measure is one or more of a parameter indicative of: an average, a median, a mode, variance, standard deviation or peak to peak variation pressure.

According to a further aspect the controller monitors average flow when said interface is not being worn.

According to a further aspect the controller monitors gases flow fluctuation, when said interface is being worn, and compares this to the reference information According to a further aspect reference information includes combinations of gases transportation pathways and patient interfaces suitable for open CPAP treatment, and combination of gases transportation pathways and patient interfaces suitable for closed CPAP treatment.

According to a further aspect said patient interface for closed CPAP treatment is one of a nasal mask, full face mask, nasal pillow mask, tracheotomy fitting, or nares sealing nasal cannula.

According to a further aspect a patient interface for open CPAP treatment is a non-sealing nasal cannula.

According to a further aspect said operating parameter includes a pressure versus time output profile.

According to a further aspect said operating parameter includes the maximum or minimum flow rate.

According to a further aspect said operating parameter includes the maximum or minimum pressure.

According to a further aspect said operating parameter includes the humidity concentration of said pressurised gases.

According to a further aspect said operating parameter includes one of a selection of operating modes, one operating mode suitable for open CPAP patient interfaces, and another operating mode suitable for closed CPAP interfaces.

According to a further aspect said operating parameter includes one of a selection of operating modes, one operating mode that controls pressure, and another mode that controls gases flow rate.

According to a further aspect said control system, in each of said operating modes, calculates treatment efficacy and/or adherence.

According to a further aspect additional operating parameters are received via a communications connection and stored in said storage device.

According to a further aspect said operating parameter includes the temperature of gases delivered to the patient; where the temperature for an open CPAP mode is higher than the temperature for a closed CPAP mode.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

BRIEF DESCRIPTION OF THE DRAWINGS

One preferred form of the present invention will now be described with reference to the accompanying drawings in which:

FIG. 3 shows detail of the nasal cannula of FIG. 1a.

DETAILED DESCRIPTION OF THE PREFERRED EMBODIMENTS

The preferred and alternative forms of the breathing assistance apparatus of the present invention axe described below.

Figure 1A:
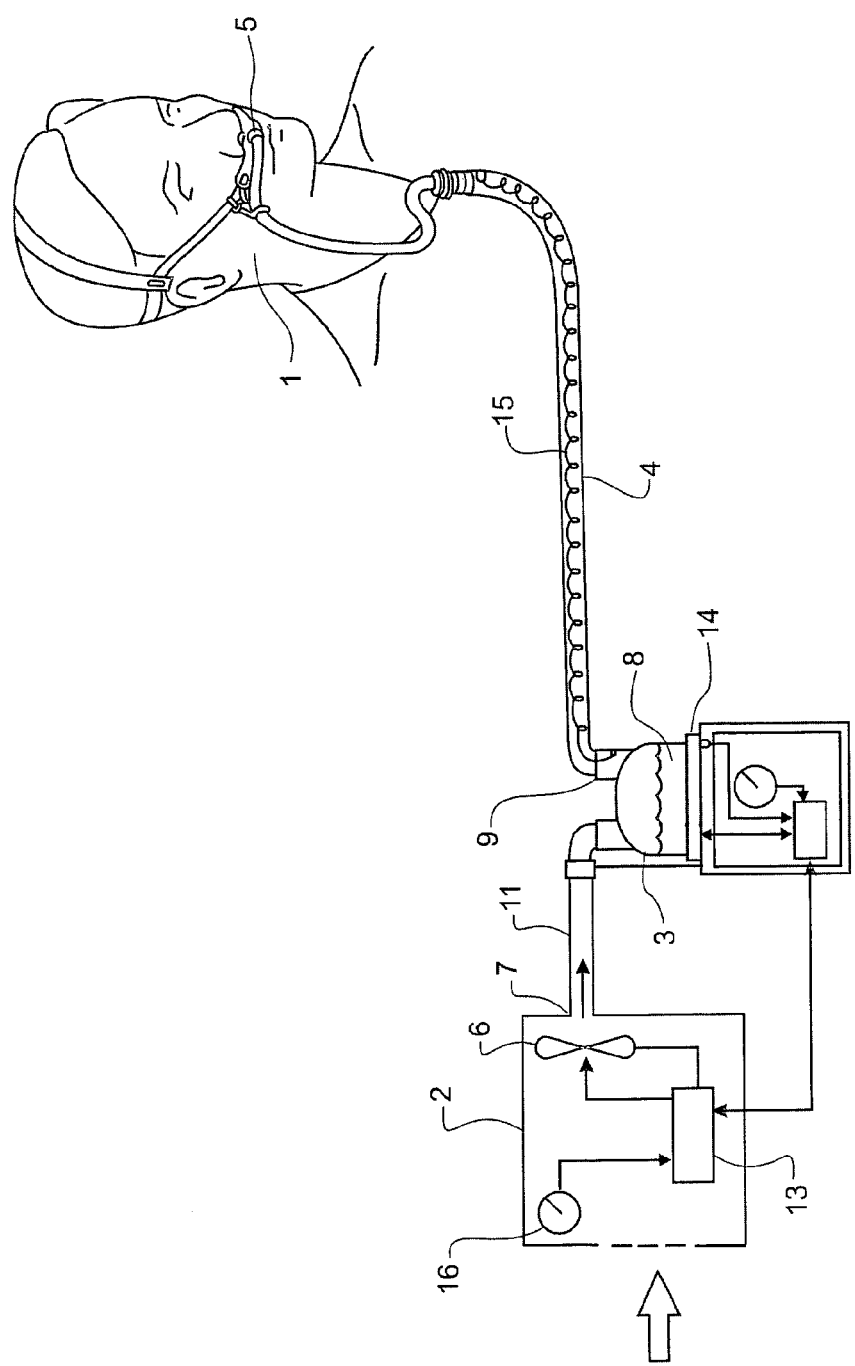
FIG. 1a shows a schematic view of a breathing assistance apparatus and a user receiving a stream of gases at a pressure above atmospheric from the apparatus by way of a nasal cannula which forms part of the breathing assistance apparatus, the breathing assistance apparatus having a flow sensor located at or close to the point of delivery of the gases to the user, and a controller which receives the readings from the flow sensor.
Figure 1B:
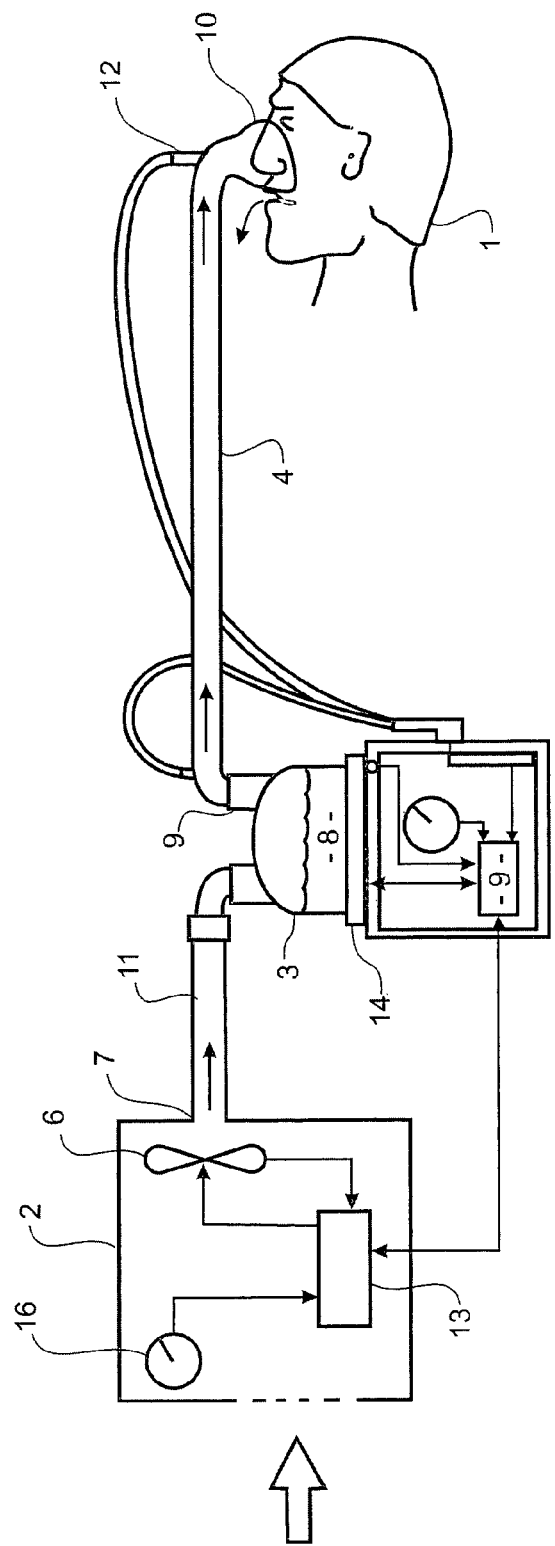
FIG. 1b shows a schematic view of a breathing assistance apparatus and a user receiving a stream of gases at a pressure above atmospheric from the apparatus by way of a nasal mask which forms part of the breathing assistance apparatus, the breathing assistance apparatus having a flow sensor located at or close to the point of delivery of the gases to the user, and a controller which receives the readings from the flow sensor.

FIGS. 1a and 1b show a schematic view of a breathing assistance apparatus, and a user 1 receiving a stream of gases at a pressure above atmospheric from the breathing assistance apparatus by way of a patient interface. The breathing assistance apparatus is generally made up of a blower unit 2, a humidifier unit 3, a conduit 4 and a patient interface.

The blower unit 2 in the embodiment has an internal fan unit 6. Air from atmosphere enters the blower unit 2 via an inlet and is pressurised by the fan unit to a pressure above atmospheric. The flow of gases provided by the fan unit 6 then exits the blower unit 2 via blower outlet 7, and enters the humidifier unit 3. The stream of gases is heated and humidified as it passes across the surface of water 8 contained in the humidifier unit 3. The heated, humidified, pressurised gases stream then exits the humidifier unit 3 via the humidifier outlet 9, and enters the conduit 4, which is connected by a first end to the humidifier outlet 9. The gases pass along the conduit 4 to the user or patient 1 and are delivered to the user 1 via the patient interface, which is connected to the second end or patient end of the conduit 4.

Other sources of breathing gases at a controlled pressure and/or flow are also within the scope of the invention. For example the gases source may be from a compressed gases reservoir or a central high pressure supply with pressure and/or flow controlled by one or more regulators.

In the embodiment shown in FIG. 1a, the patient interface is a nasal cannula 5. In the embodiment shown, the nasal cannula 5 is a side-entry cannula, with the conduit extending to one side of the nasal cannula 5. However, the cannula could be any type of nasal cannula well-known in the art. In the alternative embodiment shown in FIG. 1b, the patient interface is a nasal mask 10, of the type that is well-known in the art.

In each of the breathing assistance apparatus described above, the apparatus includes a humidifier unit 3. It should be noted that the invention could be reduced to practice using a breathing assistance apparatus which does not include a humidifier unit. Furthermore, in the embodiment of FIGS. 1a and 1b, the blower unit 2 and the humidifier unit 3 are shown as separate items, remotely located from one another, and connected by an intermediate conduit 11. A combined or integrated blower/humidifier unit could be used, where the humidifier unit and blower unit are co-located in use and connected so as to effectively form a single item. It should also be noted that a nasal cannula and a nasal mask have been shown and described, but a full-face mask or nasal pillows could be used instead of the nasal mask shown in FIG. 1b.

In this specification, the general term 'gases supply unit' will be used to refer to either a blower unit by itself, supplying gases to a connected conduit via the blower outlet 7, or to a blower unit and humidifier unit in combination, with gases supplied to the connected conduit via the humidifier outlet 9.

The blower unit 2 also contains a control unit 13. Control unit 13 is adapted to send signals to elements in the breathing assistance apparatus to change their output. For example, the control unit 13 controls the speed of the fan that forms part of the fan unit 6. The speed of the fan determines the pressure (and therefore flow) provided by the breathing assistance apparatus. In this embodiment the control unit can also control other items such as, for example, a heater plate 14 which forms part of the humidifier unit 3 in some variations, or a heater wire 15 which is located in the conduit 4 in some embodiments. When providing normal closed CPAP therapy, the fan will typically be operated by the control unit 13 at a substantially constant speed in order to provide a stream or flow of gases at a substantially constant pressure above atmospheric. However, other techniques involving active control (where the control unit adjusts the fan speed relative to a patient's breathing pattern) may also be used. Such techniques often involve the control unit slowing the fan speed as a patient exhales, and increasing the fan speed to provide a suitable CPAP pressure as they inhale. Furthermore, the control unit may control the speed of the fan according to a feedback control based on data of a parameter of the flow, typically pressure.

The control unit may be a multipurpose micro computer with stored or embedded software executing a control program. Alternatively the controller may be a single purpose micro computer or programmed logic processor such as an FPGA. Alternatively the controller and algorithm may be implemented in fixed logic circuits.

In the preferred embodiments of the present invention, the breathing assistance apparatus also has user controls 16 providing input to the control unit 13, which the user 1 or a health professional can use to alter the outputs of the breathing assistance apparatus. For example, a health professional will prescribe a therapy regime that will require a user to receive gases at a certain pressure during their sleep. The user controls 16 can be used to set the pressure of the gases delivered by the blower. The controller 13 receives the input from the user controls 16 and sets the fan speed accordingly in order to deliver the required pressure. The user controls 16 may be a simple discrete selection switch to indicate a mode of operation, or a more complex user interface that allows a user to adjust operation parameters stored in the control such as fan speed, output pressure and flow rate. In addition, the user may also be allowed to adjust data concerning the preferred humidity and delivery temperature of the supplied gases within certain limits.

In some embodiments of the present invention, the breathing assistance apparatus has a flow sensor 12. The flow sensor 12 may be built into the patient interface (e.g. the nasal cannula, the nasal mask, the full-face mask or the nasal pillows). Alternatively, the flow sensor 12 may be located at or close to the blower outlet or anywhere in the gases flow path in the blower. Signals representative of the flow rate are fed back to the controller as data of the sensed flow.

The apparatus of the present invention may also include a pressure sensor to measure the gas pressure supplied to a patient. The pressure sensor may be located at the output of the fan unit 6 or at the patient interface 5, 10. The controller can deduce the pressure at the patient interface 5, 10 by estimating the pressure drop in the conduit 4. The pressure sensor outputs a signal to the controller unit 13 the control unit 13 may use this data of the pressure to control the speed of the fan 6.

As has been outlined above, the breathing assistance apparatus can be used with a number of different types of interface. For normal CPAP operation, the operating parameters required for effective therapy may vary with the type of interface which a user prefers or has recommended to them. The pressure can be adjusted manually via the user controls 16 to set a required pressure. The controller 13 will control the fan unit 6 to provide the selected pressure. However, when different types of interface, or conduit, or both in combination are connected to the blower unit, the gases flow rate through the interface will be different depending on the specific conduit or interface which is connected.

CPAP therapy is the most common form of treatment that is initiated when a patient is diagnosed for obstructive sleep apnea-hypopnea syndrome (OSAHS). However, studies have shown that many patients are non-adherent to CPAP treatment. Non-adherence to treatment can be attributed to mask-related issues including pressure or airflow related issues and problems related to nasal delivery. Non-adherence to treatment may also be related to headgear issues including the headgear being too tight or cumbersome, or to inconvenience of masks, or to spousal intolerance.

Traditional PAP therapy methods involve a nominally sealed mask. The mask seals to the face of the user, but typically a fixed or variable leak outlet is provided in the mask body Or in a close portion of the supply conduit. An alternative is high-flow therapy (HFT). HFT is being used in clinical settings and is being applied across a range of age groups and varieties of disease conditions. The high flow rates of HFT are typically delivered via an open nasal cannula interface system. For HFT, humidification of the breathing gases is important. Preferably the supplied inspiratory gases are warmed to body temperature and humidified to at least 70% saturation. In contrast, CPAP devices tend to deliver gases at a relatively lower temperature. For CPAP, the temperature is typically limited to around 32 degrees so as to not exceed skin surface temperature, which may cause discomfort to the patient. However, that notwithstanding, an HFT device may allow the user some control over the temperature of the delivered gases to increase comfort. Properly conditioned gases provide for patient comfort and minimize deterioration of nasopharyngeal structures. HFT is sometimes referred to as humidified high-flow nasal cannula (HHFNC) therapy. For the purpose of this specification, traditional CPAP therapy will be referred to as "closed CPAP" and high flow therapy will be referred to as "open CPAP".

The patient interfaces intended to provide closed CPAP therapy (e.g. interfaces intended to seal against the face of a user, such as a nasal mask, a full-face mask, or nasal pillows) will have a different flow rate profile than a nasal cannula providing 'open' CPAP therapy. Open CPAP therapy does not require the nasal cannula to seal against the nostrils of a user. The present invention recognises that there are characteristic differences in the flow profiles between interfaces which are intended to provide sealed or closed CPAP therapy and interfaces which are intended to provide unsealed or open CPAP therapy. A system which uses an unsealed interface instead of a sealing interface may also use a conduit of a different internal diameter to connect between the static units (e.g the blower and humidifier) and the user interface. Where reference is made in this specification to an interface, this can mean any one of the following: a mask (full-face or nasal) by itself, a nasal cannula interface by itself, or either of the preceding examples with a gases supply conduit also connected. We also use the term supply path to refer to the combination of the patient interface with the gases supply conduit.

Open CPAP treatment or treatment with nasal insufflation or 'trans nasal insufflation' (TNI) is based on the principles of HFT where an open nasal cannula system is used to deliver high flow rates to the nares of a patient to alleviate the symptoms of obstructive sleep apnoea-hypopnea syndrome (OS-AHS) or upper airway resistance syndrome (UARS). It has been shown in the art that a linear increase in expiratory pharyngeal pressures (EPP) is possible with increasing flow rates. For example, EPP increased from 0.8-7.4 cmH2O during mouth closed and from 0.3-2.7 cmH2O during mouth open, for flow rates from 0-60 L/min.

The preferred embodiment of the present invention is a single blower unit, optionally combined with a humidification unit, to be capable of delivering both closed CPAP (which operates to achieve or deliver a prescribed pressure) and open CPAP therapy (which operates to achieve or deliver a prescribed flow). Furthermore, the preferred embodiment of the present invention has a pressure and flow generator that has the ability to detect the type of interface (CPAP mask or open CPAP nasal cannula) connected at the end of the breathing circuit. Subsequent to this detection the controller may adjust the operating parameters or automatically switch between CPAP and open CPAP delivery modes depending on the interface detected at the end of the breathing circuit.

According to an aspect of the present invention, determination of the supply path is made from measured characteristics of the gases flow. However, in less preferred embodiments applicable to other aspects of the invention, determination may be made based on other physical characteristics of the supply path or based on specific identification characteristics of the supply path. For example, the controller may determine the supply path based on the electrical resistance of an included heater wire; or the controller may determine the supply path by sensing an identity from contacts on the conduit connector or by interrogating an included RFID tag.

Open CPAP treatment promotes adherence to the treatment regime due to the nasal cannula being more comfortable for a user. Physicians may also choose to first prescribe open CPAP therapy to a patient sensitive to comfort issues with closed CPAP therapy. The physician may choose to switch the patient to closed CPAP treatment when the patient is comfortable with open CPAP treatment. A patient may also wish to use open CPAP for part of the night before switching to traditional CPAP therapy for the remainder of the night, or vice versa. This approach could be preferred due to the relative comfort provided by open CPAP over traditional CPAP and hence the patients may find it easier to fall asleep on the open CPAP system. Switching CPAP treatment regimes would normally require the use of separate open and closed CPAP systems which will involve a high cost.

Further, the pressure demands of OSAHS patients may change over time and a physician may find that the pressure requirements for a patient initially prescribed CPAP therapy have altered over time and that they can be successfully treated with open CPAP. Similarly, a patient initially prescribed open CPAP may require higher pressures and require a CPAP device. Again, switching devices will involve a high cost and may therefore be prohibitively expensive:

In some circumstances, the blower unit 2 (and humidifier unit 3) may be re-used with another user, or a user may change from closed or sealed therapy to open or unsealed therapy. A different combination of conduit and interface may be connected to the blower/humidifier in order to provide a stream of pressurised gases to a user.

As has been outlined in relation to the prior art, several ways or methods have been suggested in which the blower unit can adjust the output in response to having a new or different item or items connected to it. All of these methods rely on a component to provide a physical identification—for example, a unique connector, a resistor having a known value, or an RFID tag which is associated with the component and which contains data which allows the system to adjust to an appropriate output.

In contrast, one aspect of the present invention uses the physical characteristics of the supply path itself to determine the type of connected interface. For example, the controller may examine the flow rate which a particular interface type and conduit type in combination exhibits when connected to a particular blower unit with the fan running at a particular speed in order to produce a set output pressure. In the preferred embodiment of the invention the controller of the blower unit senses the flow characteristics of the interface to which the blower unit is connected, determines what the interface is from the flow and pressure characteristics and automatically switches or adjusts the output according to predetermined flow characteristics that best suit the connected interface. The flow and pressure characteristics of the connected breathing tube and patient interface are thereby sensed by the sensor and this date is used by the controller to determine the appropriate flow and pressure for CPAP therapy.

The sequence essentially taken by the preferred blower controller is to read the pressure/flow signal from the sensor. It will then calculate (a) long-term average value of the flow and (b) the flow/pressure fluctuation of the signal over some time period. The inventors have found the combination of (a) and (b) unique to the interface and conduit type connected to the blower. The controller uses this information to predict the interface and conduit type.

The algorithm does not need to operate only when the interface is not worn. Using characteristics (a) and (b) the control algorithm is able to predict the interface and conduit type in other scenarios (i.e., interface worn, not worn, blower ON or OFF etc.). This increases the robustness of the algorithm as the user does not have to wait for a certain time period for the control algorithm to determine what type of interface is connected. Therefore, the automatic detection and switching process can be completely transparent to the user.

When a supply path is not connected to the output of a blower unit, the pressure sensor reading will typically read close to atmospheric pressure. Similarly, a flow sensor (if one is present on the blower unit itself) may read a relatively high flow rate, for a given fan speed, when there is no interface connected which would otherwise provide a flow restriction. When a supply path is connected to the output of the blower unit, the increased resistance to flow will cause the pressure sensor to typically read at a higher pressure. Similarly, the flow sensor may read a flow rate below that expected for an unrestricted fan.

Figure 2:
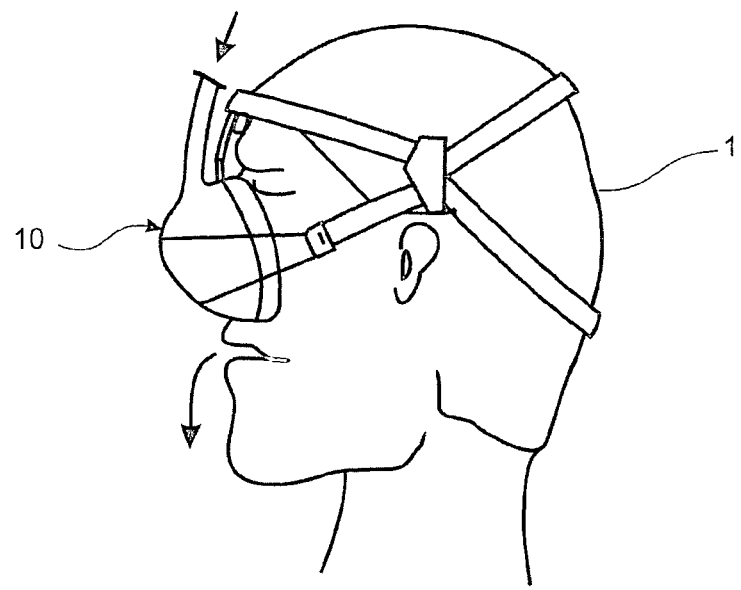
FIG. 2 shows a close-up view of the user of FIG. 1b, with detail of the nasal mask also shown.
Figure 3:
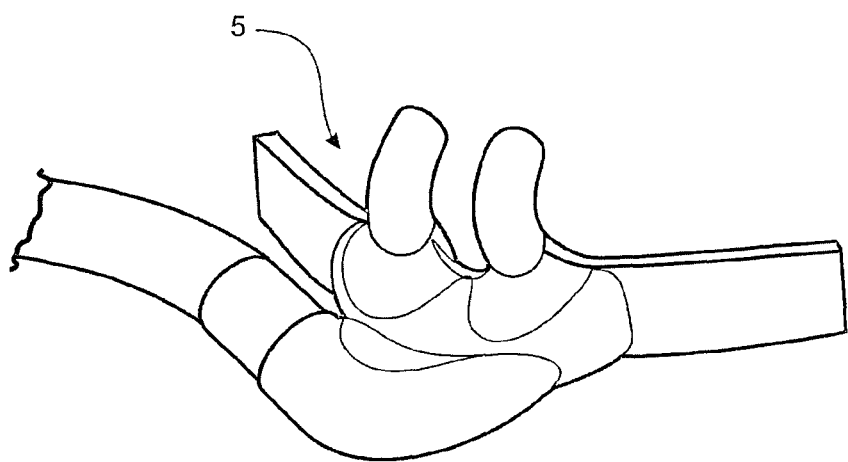
Figure 4:
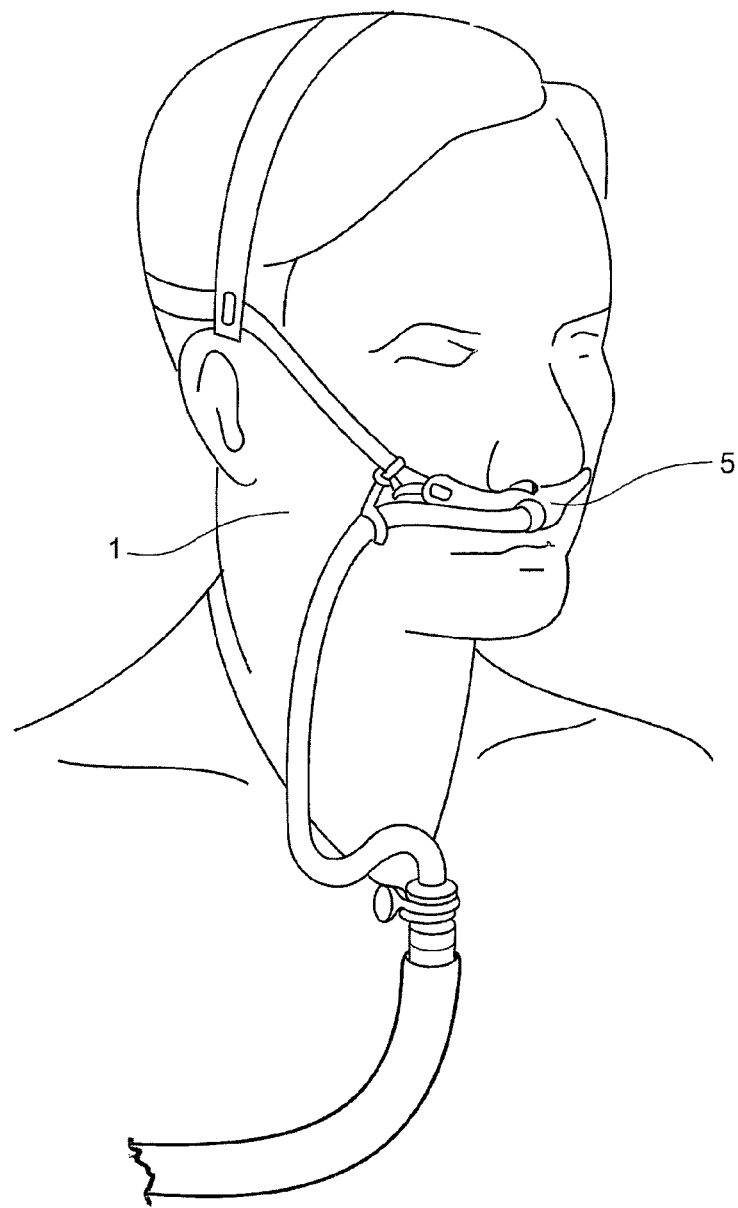
FIG. 4 shows further detail of the nasal cannula of FIGS. 1a and 3 in use.

An open CPAP interface, as shown in FIGS. 3 and 4, typically consists of a high resistance circuit whereas closed CPAP, as shown in FIG. 2, typically utilizes a low resistance circuit. This is due to the characteristic nature of the open CPAP nasal cannula which has a much smaller internal cross-sectional area than a closed CPAP delivery tube and mask combination. For example, an open CPAP interface has approximately a 78 $mm^2$ cross-sectional area through which gases can pass, compared to a closed CPAP interface having approximately a 380 $mm^2$ cross-sectional area.

The smaller cross-sectional area of the open CPAP interface poses a higher resistance to flow. For a given driving pressure, and when the interface is not being worn by a user, an open CPAP interface fitted with a nasal cannula delivers a lower flow rate than a closed CPAP interface fitted with a mask. For example, at a set pressure of 6 cMH20, an open CPAP system delivers a total flow rate of approximately 45 L/min of leak flow (with a Fisher & Paykel Healthcare 400502 large nasal cannula) compared to a flow rate of approximately 74 L/min of leak flow for a closed CPAP system utilizing a Fisher & Paykel Healthcare FlexiFit 407 NIV interface mask. The total flow rate through the system is one characteristic that can be used to determine whether an open CPAP interface or a closed CPAP interface is connected to the blower unit.

Another characteristic feature that the controller may use to detect whether an open CPAP interface or a closed CPAP interface is connected to the blower unit is the difference between the pressure fluctuation and flow fluctuation that occurs during the inspiration-expiration cycle (IEC). A small fluctuation of approximately 15-20 L/min at a set pressure of 6 cMH2O can be observed during the IEC when an open CPAP interface is being used. The flow fluctuation, or swing, can be attributed to the non-sealing nature of the open CPAP interface cannula which does not attempt to maintain a constant pressure at the nares. In contrast, there is a much larger flow fluctuation of approximately 50-60 L/min at a set pressure of approximately 6 cMH2O when a closed CPAP mask is used. This is due to the tight seal around the mask which maintains the delivered pressure. If the mask seal is compromised and air leaks occur, the IEC flow fluctuation decreases with increasing leak. The controller can use this relationship to differentiate between a reduction in flow fluctuation due to mask leak and the reduction in flow fluctuation due to the use of an open CPAP nasal cannula. The total system flow rate is much lower for an open CPAP system than for a closed CPAP system with a leaky mask.

The controller could alternatively use pressure fluctuation. If the controller is operating in a flow controlled mode, which can be a useful mode for delivering open CPAP, the controller can look at the fluctuations in the output of a pressure sensor in communication with the gas supply path, or at fluctuations in the power applied to the blower motor. An open CPAP nasal cannula will exhibit smaller fluctuations than the closed CPAP interface.

Figure 6:
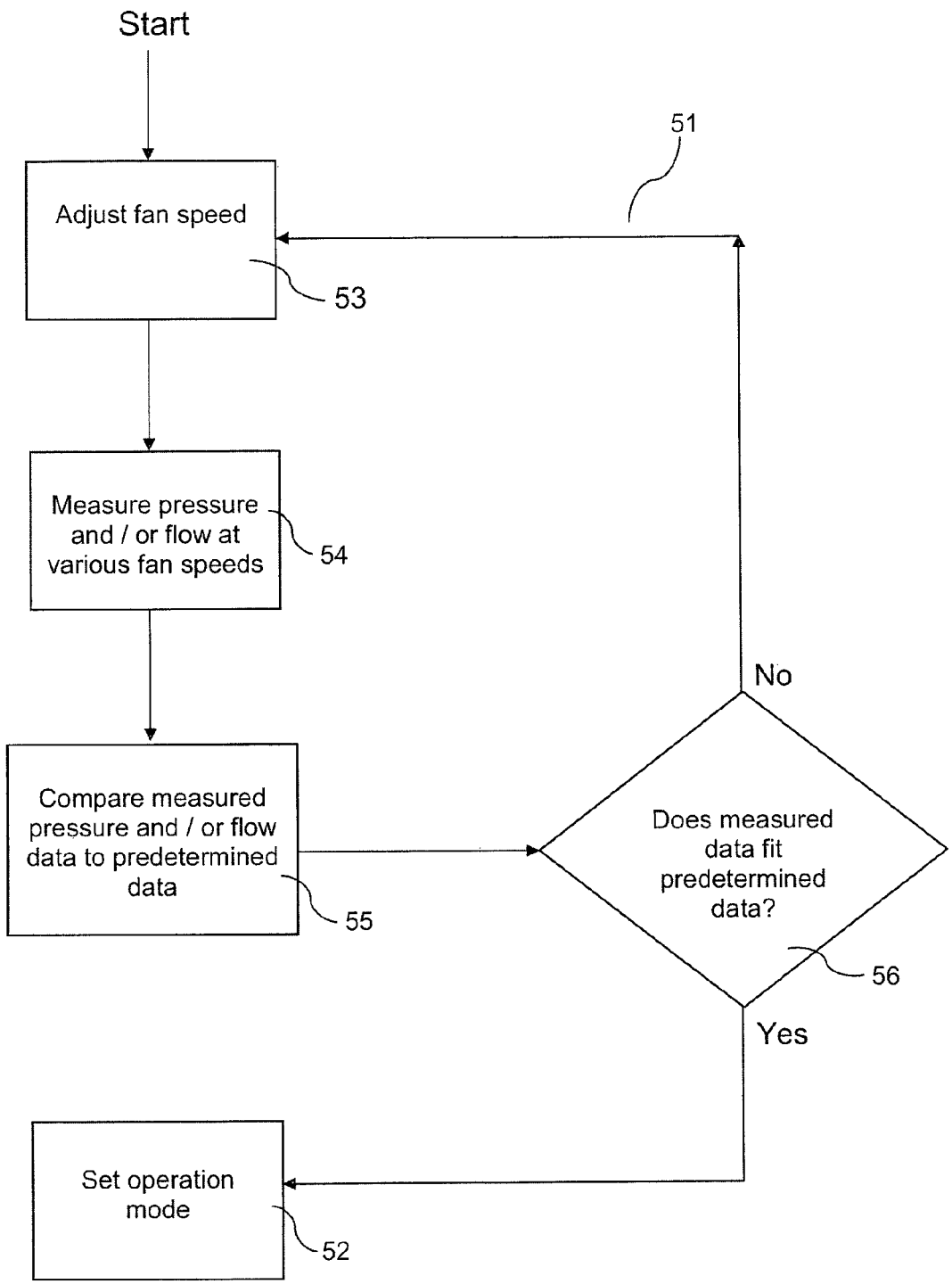
FIG. 6 shows a schematic diagram of the decision process by which the controller of the preceding figures receives data and produces an output in response.

The controller may initiate a test mode 51 when it detects an interface has been connected to the output of the blower unit. The test mode 51 is illustrated in more detail in FIG. 6.

In the first step 53 the controller operates the blower with the interface connected and samples data related to the gases flow.

At step 54 the controller analyses the flow and pressure data at each of the fan speeds. Alternatively, the second step may be to analyse either the flow or the pressure data. For example, when a patient interface connection with the blower unit is detected, the pressure data may be immediately indicative of what sort of interface is connected. As noted above, an open CPAP interface typically has a small diameter conduit connecting the interface to the blower unit. Using the data from the pressure sensor the controller means immediately determine that an open CPAP interface is connected if the controller determines that the data indicates an increase in pressure that corresponds to having a small conduit connected to the output of the controller unit. Alternatively the blower may examine the average flow and pressure signals or fluctuations in the flow signal.

At step 55 the controller compares (at 56) the flow and pressure sensor data to a set of stored values. Typically the different types of patient interfaces will exhibit different flow and pressure values across one or more fan speeds. If the measured data does not fit any stored profile information, the controller may repeat steps 53 to 55 or the controller may revert to the detection mode 50. This circumstance may indicate that the user has not properly connected a new patient interface, or has connected the interface, but is not yet wearing the mask. Alternatively, where the controller finds a match, or substantial alignment of measured and stored data, the controller will set the operation mode 52 of the blower unit to control the fan speed according to the type of connected interface, or set a mode of operation according to the type of interface determined by the algorithm.

Figure 5:
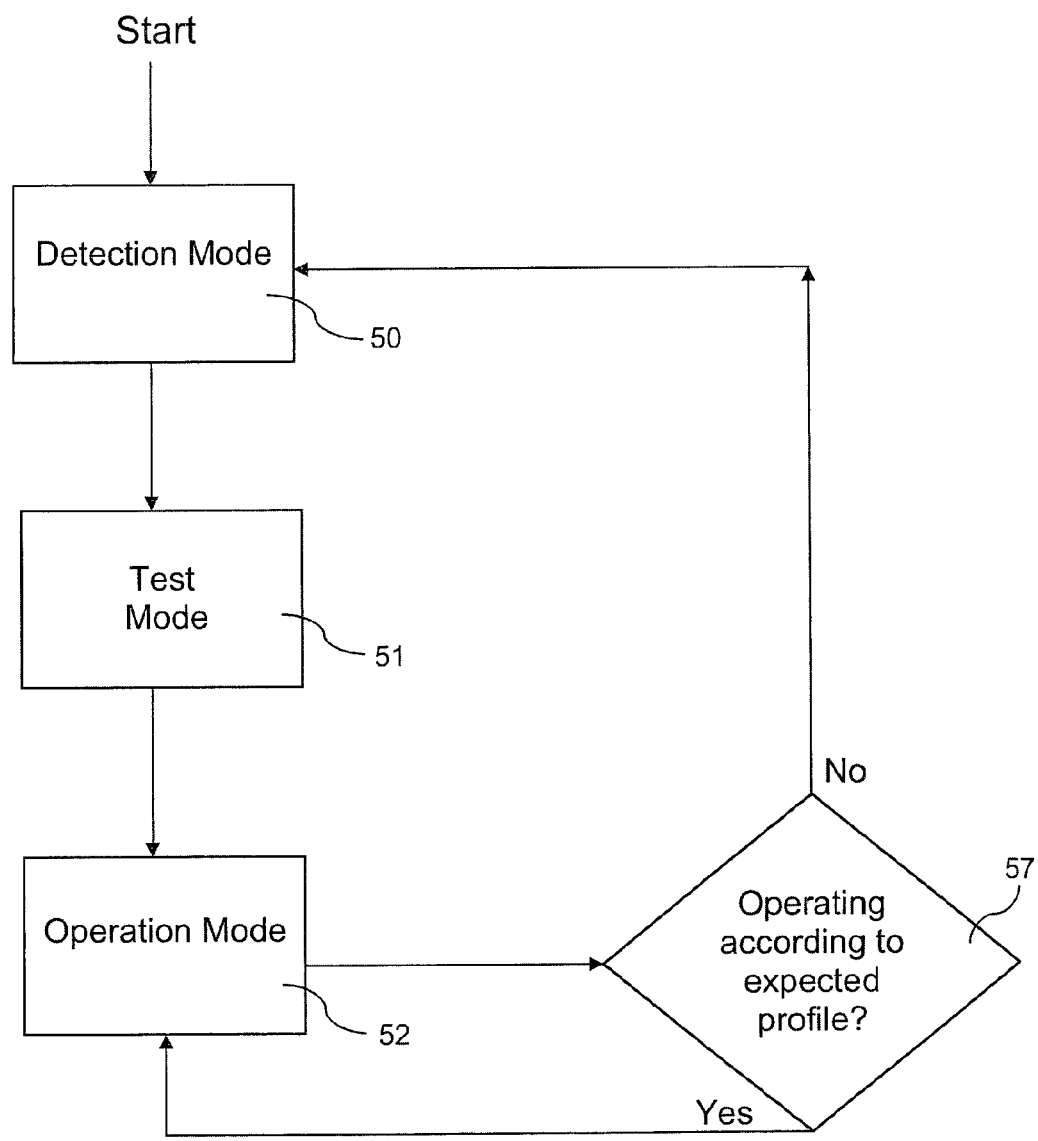
FIG. 5 shows a schematic diagram of the decision process by which the controller of the preceding figures operates the breathing assistance apparatus.

Referring again to FIG. 5, controller will change or alter the operation mode 52 according to the type of interface that has been determined by the control strategy. For example, the controller will typically set the operating mode for closed CPAP therapy to deliver a pressure range of 4 to 20 cmH$_2$O, which will typically see flow rates of up to or exceeding 40 L/minute. However, the controller may be configured to set an operational flow rate range, instead of a pressure range. In another example, the controller will typically be configured to set the operating mode for open CPAP therapy to deliver flow rates of 20 to 40 L/minute, which will typically require a pressure range of approximately 4-6 cmH$_2$O. However, the controller may be configured to set an operational pressure range, instead of a flow rate range. The controller may be configured to set the fan speed according to the pressure and/or air flow requirements, as dictated by the operation mode best suited to the detected interface.

In the preferred embodiment of the invention the controller of the blower unit will switch between two operating modes according to the detected interface. Switching between the two delivery modes will primarily entail delivering either (a) a fixed (or controlled) pressure (or alternatively automatically titrating the pressure depending on patient needs) when the device is in 'closed CPAP' mode or (b) a fixed (or controlled) air flow rate (or automatically titrating the flow rate to suit patient needs) when in 'Open CPAP' mode. Preferably, when a closed CPAP interface is determined as being connected, the controller controls the output of the blower to provide a substantially fixed or controlled pressure. Additionally, when an open CPAP interface is determined as being connected, the controller controls the output of the blower unit to provide a substantially fixed or controlled gases flow rate.

The controller may be programmed to periodically run a check, at step 57, to ensure the system is behaving as expected. The check may include, for example, comparing the current speed of the fan against an expected range of pressure and flow readings. If the range falls outside predetermined limits, the controller may then revert to the detection mode 50 to reassess the connected interface. The controller may further include a counter to monitor the number of occasions the limits are exceeded, and revert only after the limits are exceeded numerous times. This may account for momentary abnormalities in the system.

The controller is preferably configured to increase the supplied humidity, for example by commanding an increase in power to the humidifier heater plate, when switching from closed CPAP to open CPAP mode. This ensures the relatively high flow rates needed for open CPAP are adequately humidified. Similarly, the humidity is preferably decreased by the controller when switching from open CPAP to closed CPAP modes. The controller is preferably configured to increase the temperature of the delivered gases when switching from closed CPAP to open CPAP. For example, the controller can command an increase in the power to a heater in the supply path. The patient can tolerate a higher gases temperature in gases supplied direct to the nares than to a face mask. Similarly, the temperature is preferably decreased in switching from closed CPAP to open CPAP modes. If the controller can make a more detailed conclusion on mask type and distinguish different closed CPAP interfaces then this temperature response may be made according to determinations between direct nasal interfaces and mask type interfaces rather than between open CPAP and closed CPAP.

The general profiles of the most commonly used types of interface are, in the preferred embodiment, pre-loaded into the memory of the controller 13. When an interface assembly (a conduit and an interface—e.g. conduit 4 and nasal mask 10) is connected to the rest of the breathing assistance apparatus, the controller controls the blower unit 2 to provide a gases flow along the interface assembly, and the flow sensor 12 provides a reading to the control unit 13. The control unit 13 recognises the type of interface which is being used, based on company the received sensor data to the stored flow profiles, and can generate an appropriate output accordingly. A user or health professional can, if necessary make manual adjustments to this profile to optimise the therapy. These adjustments can also be saved in the memory of the controller as the optimal values to which it should switch on detection of an interface type—they can replace the default values if necessary.

The memory of the controller 13 may be a removable device, such as a flash memory, static ram or CD-ROM, and interface by serial connection or similar protocols. The memory device may be purchased separately or together with a new type of patient interface and preferably a memory device containing flow and pressure information will be provided with a newly purchased patient interface. Alternatively, a connection between the controller and a remote facility can be made by wired or wireless communication to facilitate manual adjustments or upgrades from a remote location. For example, an internet connection or mobile communications system may be established to remotely connect the control system blower unit to a remote upgrade facility. The user interface on the blower unit may facilitate communication between local or remote data and control sources.

Further functions of the controller include recording information relevant to the machine usage and therapy. For example, the controller also preferably facilitates detection and recordal of 'sleep disordered breathing' events. Such events include apnoeas, hypopnoeas, respiratory effort related arousals, flow limitations and 'wake from sleep' events. The controller may be configured to record the time, date and duration of such events. The controller may also record the time, date and duration that each of the treatment types or modes is operated for, or statistically informative information such as maximums, minimums, average, median, and mode values of pressure and gases flow rate readings. Another function of the controller is the calculation and recording of an efficacy parameter, such as the apnoea-hypopnoea index (AHI) or respiratory disturbance index (RDI). According to one invention herein the controller records data to identify the determined supply path as part of the efficacy and compliance data.

Calculation of an efficacy parameter may require the use of more sensitive flow or pressure sensing devices than are commonly used for generally sensing properties of the gases output from the blower unit. In such cases, a secondary flow or pressure sensing device may be provided with fluid connection to the breathing gases. The controller may switch the secondary sensor into the breathing circuit, or at least actively begin to monitor the secondary sensor in a manner that ensures normal operation of concurrent functions of the blower unit.

The controller may adjust or substitute the algorithms used for determining occurrence of events according to the determined supply path.

All of the calculated and recorded data in the controller is preferably stored on a removable media storage device. Alternatively, the data could be stored in fixed memory and downloaded to a separate memory device or remote server by an appropriate communications connection. The recorded data can also be used by a physician or other professional institution to determine whether a patient has undertaken sufficient therapy.

Providing the capability for a pressure/flow generator to automatically switch between open CPAP and CPAP delivery modes depending on the interface connected at the end of the delivery tube will provide a new approach for physicians to introduce OSAHS patients to traditional CPAP therapy via the use of an open CPAP system on a temporary basis. A large proportion of patients diagnosed with OSAHS refuse CPAP therapy at the outset due to mask and pressure related issues with CPAP therapy. However, open CPAP allows a physician to help a patient adapt to CPAP therapy via the open CPAP system, and it is generally a much more comfortable system for a patient new to CPAP therapy. The system will enable the patient to spend a proportion of each night on open CPAP and gradually transition to conventional CPAP therapy once they are able to tolerate CPAP. In addition, the combined open/closed CPAP system will be more flexible and allow the physician to change prescribed delivery modes without the purchase of additional pressure/flow generators.

Changing the mode of operation of the CPAP machine may be restricted by consideration of conditional elements. Such elements may include whether a treatment regime has been administered for a prescribed amount of time, or whether a calculated efficacy parameter indicates the mode can be changed. Other conditional parameters include the input of a unique code or identifier that effectively 'unlocks' previously unavailable functions. The status of such a conditional parameter can be communicated to a user by a graphical indication on the interface of the blower unit.

The ability of the device to automatically detect the interface connected at the end of the breathing tube and change the delivery mode appropriately will also remove the burden of manually changing the delivery mode from closed to open CPAP and vice versa using a manual method such as pressing a button on the pressure/flow generator. Relying on the patient to press the appropriate button has an additional disadvantage of being subject to errors made by the patient in selecting the appropriate delivery mode. In addition, having the ability for the device to automatically switch to the appropriate delivery mode depending on the interface connected to the breathing tube also makes the system easier to use for the patient.

Existing blower units that do not support automatic switching of flow profiles often have the capability for the controller software, or firmware, to be changed or updated. It is envisaged that exiting blower units can be updated to support automatic flow profile switching, including steps necessary to detect the type of interface connected to the blower unit by sensing flow data. Further, it is envisaged the software or firmware updates are facilitated by connection to a remote resource, such as a database. A connection can be made by wired or wireless communication. For example, an internet connection or mobile communications system may be established to remotely connect the control system blower unit to a remote upgrade facility.

We claim:

1. Breathing assistance apparatus comprising:
a gases supply unit adapted to, in use, deliver a stream of pressurised gases, an outlet for supplying, in use, the pressurised gases stream to a supply path including a flexible self-supporting gases transportation pathway and a patient interface;
a control system associated with the gases supply unit adapted to receive data of at least one information parameter from at least one sensor, said at least one information parameter comprising a parameter of a flow of gases from said outlet, said control system containing reference data, said control system comparing said received data to said reference data, and determining said supply path based on said comparison,
wherein said reference data comprises a plurality of flow parameter profiles and individual flow parameter profiles corresponding to individual supply paths and
wherein determining said supply path based on said comparison comprises identifying at least one of the plurality of flow parameter profiles that substantially aligns with said received data.

2. Breathing assistance apparatus as claimed in claim 1, wherein said determining the supply path further comprises determining if the patient interface is a non-sealing cannula or a sealing mask.

3. Breathing assistance apparatus as claimed in claim 1, wherein said control system adjusts an operating parameter based on said determined supply path.

4. Breathing assistance apparatus as claimed in claim 3, wherein said control system adjusts the operating parameter between a condition suitable for open CPAP and a condition suitable for closed CPAP.

5. Breathing assistance apparatus as claimed in claim 3, wherein said control system adjusts a first operating mode that controls pressure for closed CPAP, and a second mode that controls gases flow rate for open CPAP.

6. Breathing assistance apparatus as claimed in claim 3, wherein said operating parameter includes the humidity concentration of said pressurised gases stream.

7. Breathing assistance apparatus as claimed in claim 3, wherein said operating parameter includes a humidity for closed CPAP that is lower than a humidity for open CPAP.

8. Breathing assistance apparatus as claimed in claim 1, wherein said control system is adapted to store information indicative of sleep disordered breathing events including one or more of an apnoea, a hyperpnoea, a respiratory related arousal, a flow limitation, or a wake from sleep event, associated with each determined supply path.

9. Breathing assistance apparatus as claimed in claim 1, wherein said at least one information parameter includes a parameter indicative of an output pressure of said gases supply unit.

10. Breathing assistance apparatus as claimed in claim 1, wherein said at least one information parameter includes a parameter indicative of the output gas flow rate of said gases supply unit.

11. Breathing assistance apparatus as claimed in claim 1, wherein said at least one information parameter includes a parameter indicative of a motor speed of said gases supply unit or a motor current of said gases supply unit.

12. Breathing assistance apparatus as claimed in claim 1, wherein said reference data includes a statistically informative measure of flow for a pressure over a time period.

13. Breathing assistance apparatus as claimed in claim 12, wherein said statistically informative measure is one or more of a parameter indicative of: an average, a median, a mode, a variance, a standard deviation or a peak to peak variation pressure.

14. Breathing assistance apparatus as claimed in claim 1, wherein said reference data includes a statistically informative measure of pressure for a flow over a time period.

15. Breathing assistance apparatus as claimed in claim 14, wherein said statistically informative measure is one or more of a parameter indicative of: an average, a median, a mode, a variance, a standard deviation or a peak to peak variation pressure.

16. Breathing assistance apparatus as claimed in claim 1, wherein said control system monitors average flow when said interface is not being worn.

17. Breathing assistance apparatus as claimed in claim 1, wherein said control system monitors gases flow fluctuation when said interface is being worn and compares this to the reference data.

18. Breathing assistance apparatus as claimed in claim 3, wherein said operating parameter includes a pressure versus time output profile.

19. Breathing assistance apparatus as claimed in claim 3, wherein said operating parameter includes a maximum flow rate or a minimum flow rate.

20. Breathing assistance apparatus as claimed in claim 3, wherein said operating parameter includes a maximum pressure or a minimum pressure.

21. Breathing assistance apparatus as claimed in claim 3, wherein said operating parameter includes a temperature of gases delivered to a patient, wherein a temperature for an open CPAP mode is higher than a temperature for a closed CPAP mode.

22. Breathing assistance apparatus comprising:
a gases supply unit adapted to, in use, deliver a stream of pressurised gases, an outlet for supplying, in use, the pressurised gases stream to a supply path including a flexible self-supporting gases transportation pathway and a patient interface;
a control system associated with the gases supply unit and adapted to receive data of at least one information parameter from at least one sensor, said at least one information parameter comprising a parameter of a flow of gases from said outlet, said control system containing reference data, said control system comparing said received data to said reference data, and, based on the comparison, adjusting an operating parameter among a condition suitable for open CPAP and a condition suitable for closed CPAP and
wherein said reference data comprises a plurality of flow parameter profiles, individual flow parameter profiles correlated to supply paths suitable for open CPAP operating parameters or closed CPAP operating parameters, and
wherein adjusting said operating parameter comprises identifying at least one of the plurality of flow parameter profiles that substantially aligns with said received data.

23. Breathing assistance apparatus as claimed in claim 22 further comprising determining the supply path, which further comprises determining if the patient interface is a non-sealing cannula or a sealing mask.

24. Breathing assistance apparatus as claimed in claim 22, wherein said reference data includes a statistically informative measure of flow for a pressure over a time period.

25. Breathing assistance apparatus as claimed in claim 22, wherein said reference data includes a statistically informative measure of pressure for a flow over a time period.

26. Breathing assistance apparatus as claimed in claim 22, wherein said control system monitors average flow when said patient interface is not being worn.

27. Breathing assistance apparatus as claimed in claim 22, wherein said control system monitors gases flow fluctuation when said patient interface is being worn, and compares this to the reference data.

28. Breathing assistance apparatus as claimed in claim 22, wherein said operating parameter includes one of a selection of operating modes, one operating mode suitable for open CPAP patient interfaces, and another operating mode suitable for closed CPAP interfaces.

29. Breathing assistance apparatus as claimed in claim 22, wherein said operating parameter includes one of a selection of operating modes, one operating mode that controls pressure, and another mode that controls gases flow rate.

* * * * *